United States Patent
Roth et al.

(10) Patent No.: US 9,801,669 B2
(45) Date of Patent: Oct. 31, 2017

(54) BONE PLATE

(75) Inventors: Beat Roth, Solothurn (CH); Urs Hulliger, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 989 days.

(21) Appl. No.: 13/100,784

(22) Filed: May 4, 2011

(65) Prior Publication Data

US 2011/0301608 A1    Dec. 8, 2011

Related U.S. Application Data

(60) Provisional application No. 61/350,691, filed on Jun. 2, 2010.

(51) Int. Cl.
*A61B 17/80* (2006.01)
*A61B 17/70* (2006.01)

(52) U.S. Cl.
CPC ...... *A61B 17/8052* (2013.01); *A61B 17/7059* (2013.01); *A61B 17/8057* (2013.01); *A61B 17/8061* (2013.01)

(58) Field of Classification Search
CPC .................. A61B 17/8057; A61B 17/8052
See application file for complete search history.

(56) References Cited

U.S. PATENT DOCUMENTS

| 2005/0059971 A1* | 3/2005 | Michelson ................. 606/69 |
| 2006/0235400 A1* | 10/2006 | Schneider ................. 606/69 |
| 2008/0300637 A1 | 12/2008 | Austin et al. |

FOREIGN PATENT DOCUMENTS

| CN | 201469392 | 5/2010 |
| DE | 10 2005 042766 | 1/2007 |
| FR | 2 848 413 | 6/2004 |
| JP | 2009/502336 | 1/2009 |
| WO | 2005/018472 | 3/2005 |
| WO | 2007/014192 | 2/2007 |
| WO | 2009/023666 | 2/2009 |
| WO | 2009/058969 | 5/2009 |

* cited by examiner

*Primary Examiner* — David Bates
(74) *Attorney, Agent, or Firm* — Fay Kaplun & Marcin, LLP (57) ABSTRACT

A bone plate includes a first through hole extending through the plate along a first longitudinal axis from a proximal surface of the plate to a bone-facing distal surface thereof which, when the plate is placed on a target portion of bone in a desired orientation, faces the bone. An outer wall of the first through hole includes three wall sections provided with projections for receiving a screw head of a bone screw. The three wall sections are straight or convex.

18 Claims, 8 Drawing Sheets

BONE PLATE

PRIORITY CLAIM

The present application claims priority to U.S. Provisional Application Ser. No. 61/350,691 filed on Jun. 2, 2010 and entitled "Bone Plate," the entire disclosure of which is incorporated herein by reference.

FIELD OF THE INVENTION

The present invention generally relates to a bone plate which can be fixed to a bone by means of bone screws. More particularly, the present invention relates to a bone plate having a through hole with an internal thread to threadably receive a locking bone screw.

BACKGROUND OF THE INVENTION

Bone plates with through holes comprising a cylindrical or conical interior thread to receive a locking head bone screw are commonly used in the field of osteosynthesis. Due to the threaded connection between the head of the bone screw and the through hole in the bone plate the bone screw is firmly anchored in the through hole in the bone plate. However, one problem that can arise is that if the bone screw is not exactly coaxially inserted with respect to the through hole axis the thread of the through hole can be damaged.

SUMMARY OF THE INVENTION

The present invention relates to a bone plate being able to receive at least a central bone screw in such a way that the thread in the through hole in the bone plate is not damaged when a bone screw is inserted.

According to the present invention, described is a bone plate with a proximal surface, a bone-oriented distal surface and a through hole the wall of which has three or more straight or convex sections provided with projections such as thread or thread-like structures for receiving a screw head of a bone screw.

One of the advantages of the bone plate according to the present invention include a compact entry for setting at choice bone screws under a variable angle is provided in such a way that the thread in the through hole in the bone plate is not damaged when a bone screw is not coaxially inserted with respect to the longitudinal axis of the through hole. Furthermore, due to the configuration of a through hole with three or more straight or convex sections, a bone screw inserted through the through hole may be angled relative to a longitudinal axis of the through hole with a reduction of damage to the threads of the through hole.

In an exemplary embodiment of the bone plate, the through hole has a cross-sectional area orthogonal to the longitudinal axis with a center of the cross-sectional area being centered on the longitudinal axis and wherein each of the three or more straight or convex sections is limited by two radii intersecting each other in the center and enclosing an angle $\Omega$ which is smaller than or equal to $360°/n$ (where n is the number of straight or convex sections), as will be described in greater detail below.

In a further exemplary embodiment of the bone plate, the through hole has a cross-sectional area orthogonal to the longitudinal axis which is generally polygonal, preferably with rounded corners.

In a further embodiment of the bone plate, the through hole tapers in a direction towards a distal surface of the bone plate.

In again a further embodiment of the bone plate, the three or more straight or convex sections are radially symmetric.

In another embodiment of the bone plate, a thread or thread-like structure extends over the whole length of the three or more straight or convex sections.

In another embodiment of the bone plate, the thread or thread-like structure has a constant depth of thread within the straight or convex sections.

In yet another embodiment of the bone plate the depth of thread of the thread or thread-like structure decreases towards each end of each of the straight or convex sections.

In still another embodiment of the bone plate the depth of thread of the thread or thread-like structure decreases outside each end of each of the straight or convex sections.

In again another embodiment of the bone plate, the thread or thread-like structure extends over the whole periphery of the through hole.

In a further embodiment of the bone plate according to the present invention, the bone plate comprises two or more peripheral holes connected to and open to a through hole. The peripheral holes include a thread for receiving peripheral bone screws therein. The two or more peripheral holes are arranged peripherally around the through hole in such a way that they overlap with the through hole to form a composite hole structure able to receive two or more peripheral bone screws therein while a central bone screw is received in the through hole.

In a further embodiment of the bone plate each of the peripheral holes comprises a spherical recess penetrating partially into the bone plate from a proximal surface thereof. The advantage of this configuration is that a conventional cortex screw with an unthreaded spherical head may be introduced into such a peripheral hole at an angle relative to the longitudinal axis selected by the user.

In a further embodiment of the bone plate according to the invention, each of the peripheral holes and the through hole includes a thread for locking the screw received therein at a fixed angle.

In another embodiment of the bone plate, the peripheral holes include threading for receiving peripheral bone screws at user selected variable angles relative to the longitudinal axes of these peripheral holes while the through hole is configured to receive a central bone screw at a fixed angle.

In a further embodiment of the bone plate, the threads of the holes extend over at least half of a circumference of each of the holes.

In still a further embodiment of the bone plate, a number, N, of holes are arranged at the corners of a central through hole being generally polygonal with N corners. The polygon defined by the hole axes of the N holes, when viewed in a cross-section orthogonal to the longitudinal axis of the through hole, can be a triangle, square, pentagon or hexagon.

In another embodiment of the bone plate the fixed angle of insertion of bone screws through the peripheral holes is in the range of ±0° to ±20°, preferably of ±8° to ±15° with respect to the longitudinal axis.

In yet another embodiment of the bone plate the pitch of the threads is in the range of 0.30 to 2.00 mm, preferably in the range of 0.5 to 1.0 mm.

In again another embodiment of the bone plate the threads are multiple threads. This allows the advantage that the pitch matches the bone thread pitch.

In still another embodiment of the bone plate the centers of two adjacent holes are at a distance of 4 to 15 mm from each other.

In a further embodiment of the bone plate the diameter of the holes is in the range of 3 to 10 mm.

In again a further embodiment of the bone plate, an inscribed circle to the wall of the central through hole has a diameter of 2 to 10 mm, preferably of 3 to 7 mm.

In another embodiment according to the present invention, the bone plate comprises at least one peripheral bone screw wherein the plate is made of stainless steel and the at last one peripheral bone screw is made of a CoCr alloy or vice versa. Thus, the advantage can be achieved that since the threads are less damaged by the plate according to the invention there is also less corrosion between plate and screws.

In again another embodiment of the bone plate a hole axis of the at least one hole is not parallel to the longitudinal axis of the though hole and preferably angled relative thereto at an angle of ±5° to ±20°.

In again another embodiment the bone plate comprises more than one through hole.

In again another embodiment of the bone plate, the wall of the through hole has n=3 straight or convex sections.

In a further embodiment a bone plate is provided with a proximal surface, a bone-oriented distal surface and a through hole with a longitudinal axis connecting the proximal and distal surfaces, wherein the wall of the through hole has n≥3 non-concave sections provided with a thread or thread-like structures for receiving a screw head of a bone screw.

According to a further object of the invention a kit for bone fixation is provided comprising a bone plate according to the invention, a central bone screw and N peripheral bone screws.

In a special embodiment of the kit, the central bone screw comprises a screw head with an external thread matching the thread or thread-like structure in the through hole of the bone plate and the N peripheral bone screws comprise a screw head each with an external thread matching the thread in the N≥2 holes.

In another embodiment of the kit, the screw head of the central bone screw is conically or spherically shaped and the screw heads of the peripheral bone screws are conically or spherically shaped.

In again another embodiment the kit comprises more than one central bone screws with differently shaped screw heads and a number of 2×N peripheral bone screws with differently shaped screw heads. This configuration allows the advantage that the surgeon can select between:
- a central bone screw with a conically shaped threaded screw head that is placed at fixed angle relative to the bone plate;
- a central bone screw with a spherically shaped threaded screw head that can be placed at a variable angle relative to the bone plate;
- N peripheral bone screws with a conically shaped threaded screw head that are placed at a fixed angle relative to the bone plate; or
- N peripheral bone screws with a spherically shaped threaded screw head that are placed at a variable angle relative to the bone plate.

In a further embodiment the kit comprises a bone plate, a central bone screw with a screw head that is conically or spherically shaped and comprises an external thread and N conventional cortex screws as peripheral bone screws.

BRIEF DESCRIPTION OF THE DRAWINGS

Several exemplary embodiments of the invention will be described in the following by way of example and with reference to the accompanying drawings in which.

DETAILED DESCRIPTION

The present invention is directed to a system for the fixation of fractured or otherwise damaged bones via one or both of a variable angle insertion and a fixed angle insertion of a bone screw through a bone plate hole. Specifically, a bone plate according to the present invention is provided with a central through hole configured to receive a first bone screw therethrough at any user selected angle relative to a longitudinal axis of the through hole within a permitted range of angulation. A plurality of second bone screws may also be inserted through outlying portions of the bone plate hole, each defining a separate plate hole axis. The outlying portions of the bone plate hole are formed as substantially circular peripheral holes configured to overlap and be open to the through hole to form a composite hole having any of a plurality of shapes depending on the placement and number of the peripheral holes relative to the through hole, as will be discussed in greater detail with respect to particular embodiments. The peripheral holes may be configured with holes axes selected so that the second bone screws may only be inserted therethrough at predetermined angles relative to a surface of the bone plate. It is noted that although the peripheral holes and through holes are depicted with predetermined angles in the system of the present invention, these bone plate holes may extend through the bone plate at any angle without deviating from the spirit and scope of the present invention and may be selected to conform to the requirement of a particular procedure.

Figure 1:
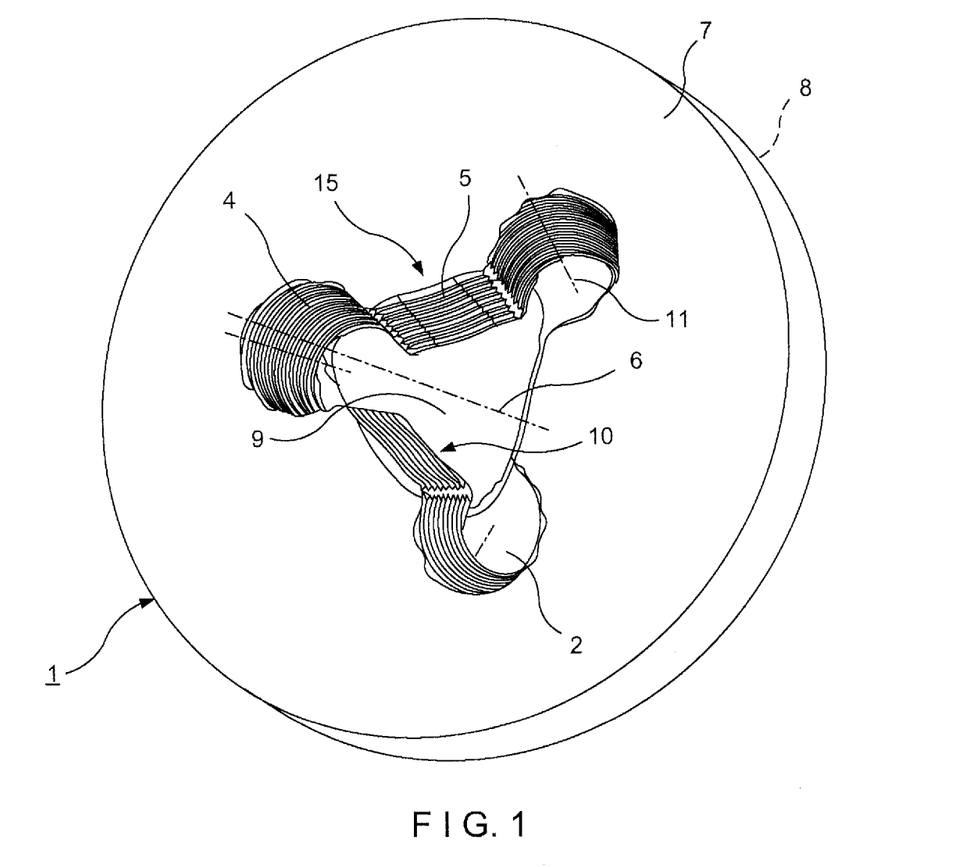
FIG. 1 illustrates a perspective view of an exemplary embodiment of the bone plate according to the present invention.

FIGS. 1 to 8 illustrate a first exemplary embodiment of the invention comprising a bone plate 1 including one through hole 9 and three partially cylindrical peripheral holes 2 arranged peripherally around the through hole 9 in such a way that they overlap with the through hole 9 and are open thereto, as will be described in greater detail below. It is noted that although the through hole 9 is depicted with a triangular cross-sectional shape, any other cross-sectional shape may be employed without deviating from the spirit and scope of the present invention. The bone plate 1 comprises a proximal surface 7 and a bone-oriented distal surface 8. The through hole 9 has a longitudinal axis 6 connecting the proximal and distal surfaces 7, 8, the longitudinal axis 6 extending orthogonally to the proximal surface 7. The through hole 9 is at least partially bordered by a wall 10 including three convex sections 15 provided with projections such as a thread 5 or thread-like structures for receiving a central bone screw 30 under a variable angle. As will be described in greater detail later, each of the three convex sections 15 of FIG. 1 is curved with a predetermined radius of curvature. In an alternate embodiment (not shown), any number and combination of the convex sections 15 may be formed with a first radius of curvature while the remainder of the convex sections 15 may be formed with a second radius of curvature.

Figure 2:
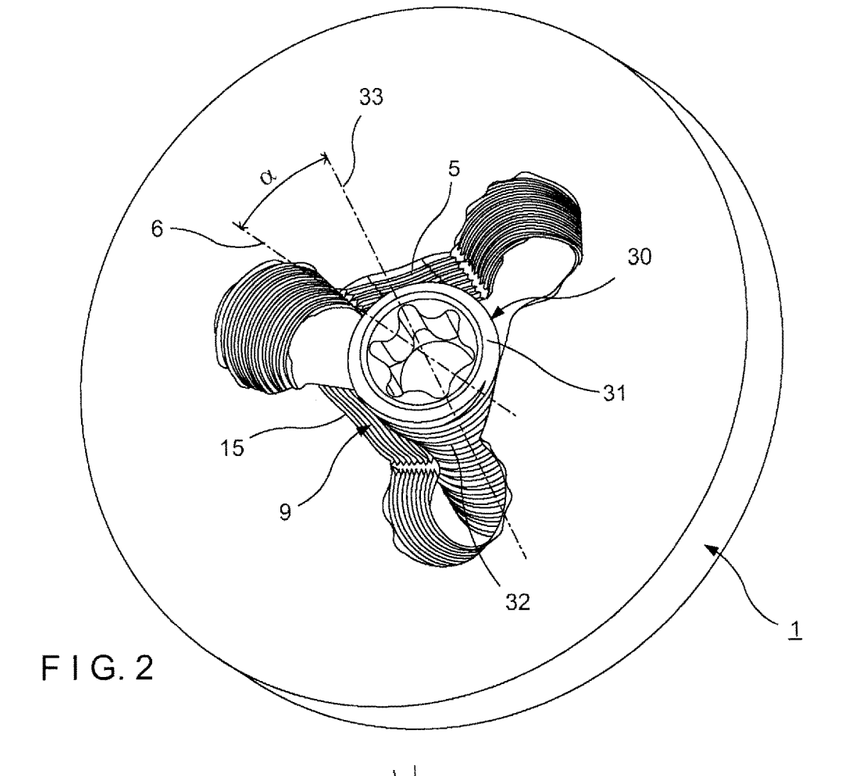
FIG. 2 illustrates the bone plate according to FIG. 1 with an inserted central bone screw.
Figure 3:
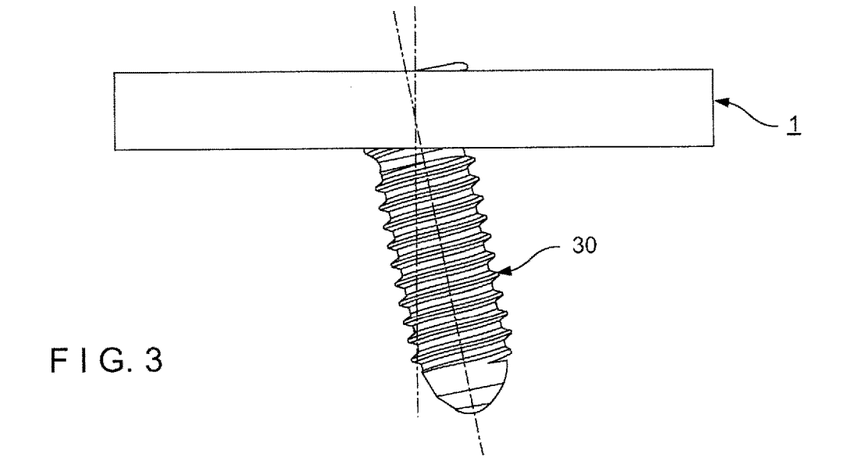
FIG. 3 illustrates a lateral view of the bone plate according to FIG. 2.
Figure 4:
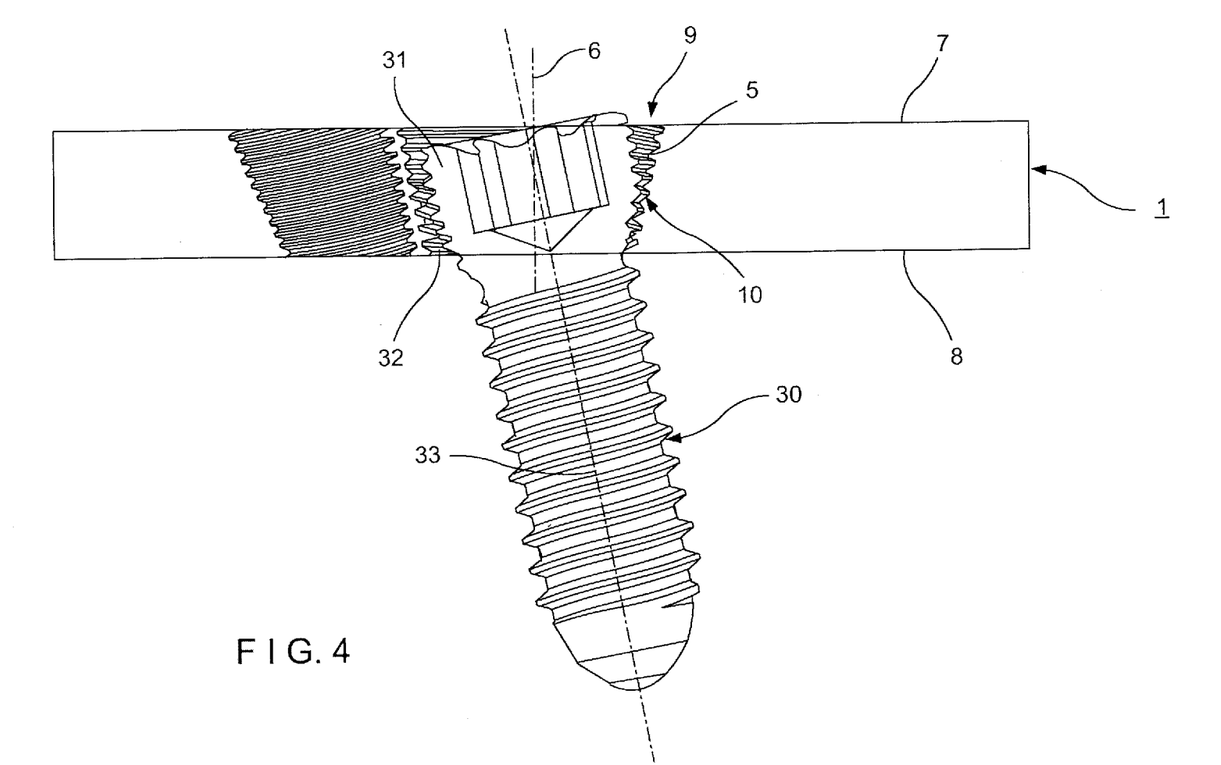
FIG. 4 illustrates a cross section through the bone plate according to FIG. 2.
Figure 5:
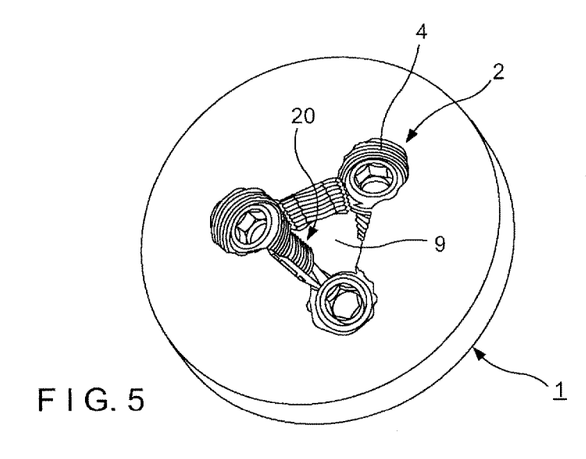
FIG. 5 illustrates perspective view onto the top of the bone plate according to FIG. 1 with inserted peripheral screws.
Figure 6:
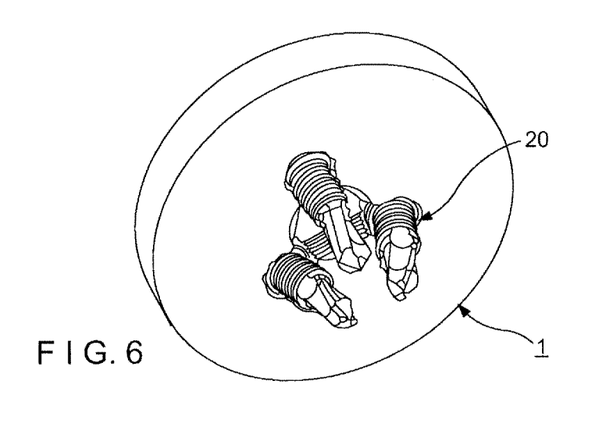
FIG. 6 illustrates perspective view onto the bottom of the bone plate according to FIG. 1 with inserted peripheral screws.
Figure 7:
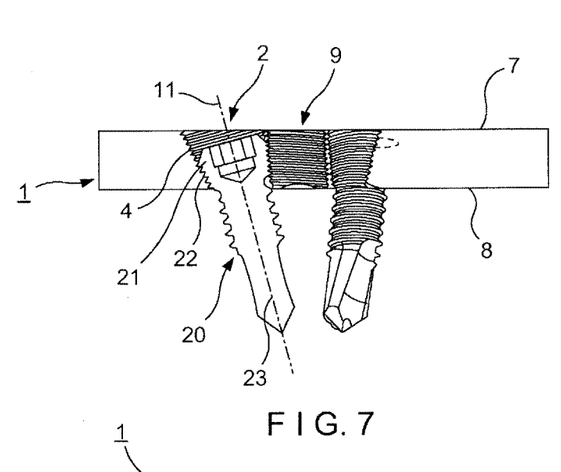
FIG. 7 illustrates a cross section through the bone plate according to FIG. 5.
Figure 8:
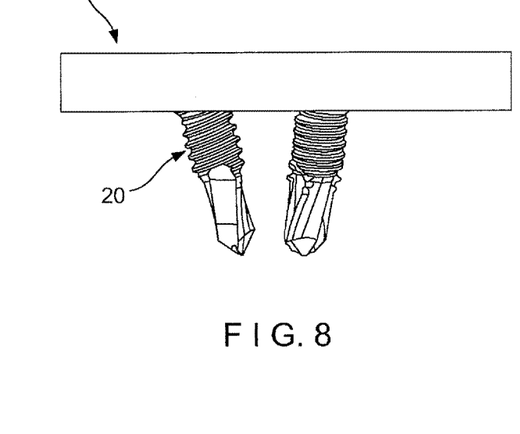
FIG. 8 illustrates a lateral view of the bone plate according to FIG. 5.

Each of the peripheral holes 2 each has a hole axis 11 extending between the proximal and distal surfaces 7, 8 and are provided with a thread 4 for receiving peripheral bone screws 20, as shown in FIGS. 6-8. The peripheral holes 2 are arranged peripherally around the through hole 9 at equal angles relative to each other. In the embodiment shown where three peripheral holes 2 are employed, the axes 11 of the peripheral holes 2, when viewed in a cross-section orthogonal to the longitudinal axis 6 of the through hole 9, define an equilateral triangle. Furthermore, the three peripheral holes 2 overlap the through hole 9 in such a way that the peripheral holes 2 and through hole 9 form a composite hole structure suitable to receive 3 peripheral bone screws 20, as shown in FIGS. 5 to 8 and/or one central bone screw 30, as shown in FIGS. 2 to 4. As shown in FIG. 5, the peripheral holes 2 each also comprise a thread 4, which, in one embodiment of the present invention, may be a multiple thread.

When viewed in a cross-section orthogonal to the longitudinal axis 6 of the through hole 9, each of the convex sections 15 is centrally positioned along a respective corner of an equilateral triangle. Each convex section 15 is convexly curved in a direction from the proximal surface 7 to the distal surface 8 so that an apex of each of the convex sections 15 is located radially outside the through hole 9. A bone screw 30 can be inserted into the through hole 9 under a surgeon selected angle so that a screw axis 33 of the bone screw 30 is offset by an angle α relative to the longitudinal axis 6 of the through hole 9. The through hole 9 of the present invention may be configured so that the bone screw 30 insertable therethrough is smaller, larger or the same size as the bone screws 20 insertable through the peripheral holes 2.

The composite hole structure therefore includes three radially symmetrically arranged convex sections 15 centrally located on the sides of an equilateral triangle and three peripheral holes 2 in the corners of the equilateral triangle. The axes 11 of the peripheral holes 2 are arranged at a distance from the longitudinal axis 6 which is dimensioned in such a way that the peripheral holes 2 overlap the through hole 9 and extend over an angle of more than 180° between their transitions to the through hole 9. The wall 10 of the through hole 9 comprises n=3 wall portions with each wall portion being limited by a transition to the periphery of a first peripheral hole 2 at one of its ends and by a transition to the periphery of a second peripheral hole 2 at its other end. In the present embodiment each convex section 15 does not extend over the whole length of the wall portion limited by the transitions. The thread 5 or thread-like structure extends over the whole length of the three convex sections 15 with a constant depth of thread. The depth of thread of the thread 5 or thread-like structure decreases between each end of the convex section 15 and each of the two transitions to one of the peripheral holes 2.

As illustrated in FIGS. 2 to 4 the through hole 9 tapers radially inward toward the distal surface 8 of the bone plate 1. A central bone screw 30 with a screw axis 33 and a screw head 31 is inserted in the through hole 9. The screw head 31 is spherically shaped and comprises an external thread 32 so that the central bone screw 30 can be inserted into the through hole at a user-selected angle α between the screw axis 33 and the longitudinal axis 6 of the through hole 9.

Instead of a central bone screw 30 comprising a spherically shaped screw head 31 with an external thread 32 a central bone screw comprising a conically shaped screw head with an external thread could be inserted into the through hole 9. In the latter case the central bone screw would be inserted into the through hole 9 at a fixed angle (e.g., with the screw axis and the longitudinal axis 6 of the through hole 9 coinciding).

As shown in FIGS. 7 and 8, the peripheral holes 2 are configured so that each of the hole axes 11 is angled at approximately 20° relative to the longitudinal axis 6 of the through hole 9. In another embodiment of the present invention, the peripheral holes 2 may be angled at any other angle relative to the longitudinal axis 6 and may optionally also each extend along different angles, as those skilled in the art will understand.

As illustrated in FIG. 7 each of the peripheral holes 2 tapers radially inward towards the distal surface 8 of the bone plate 1. A peripheral bone screw 20 with a screw axis 23 and a screw head 21 is inserted into each of the peripheral holes 2. The screw head 21 is conically shaped and comprises an external thread 22 so each peripheral bone screw 20 can be inserted into one of the peripheral holes 2 at a fixed angle with the screw axis 23 and the hole axis 11 of the peripheral hole 2 coinciding.

Instead of peripheral bone screws 20 comprising conically shaped screw heads 21 with an external thread 22, peripheral bone screws comprising spherically shaped screw heads with an external thread may be inserted into the peripheral holes 2. In the latter case the peripheral bone screws may be inserted at a user selected variable angle between the screw axis 23 and the hole axis 11 of the peripheral hole 2.

Figures 9, 10, 11:
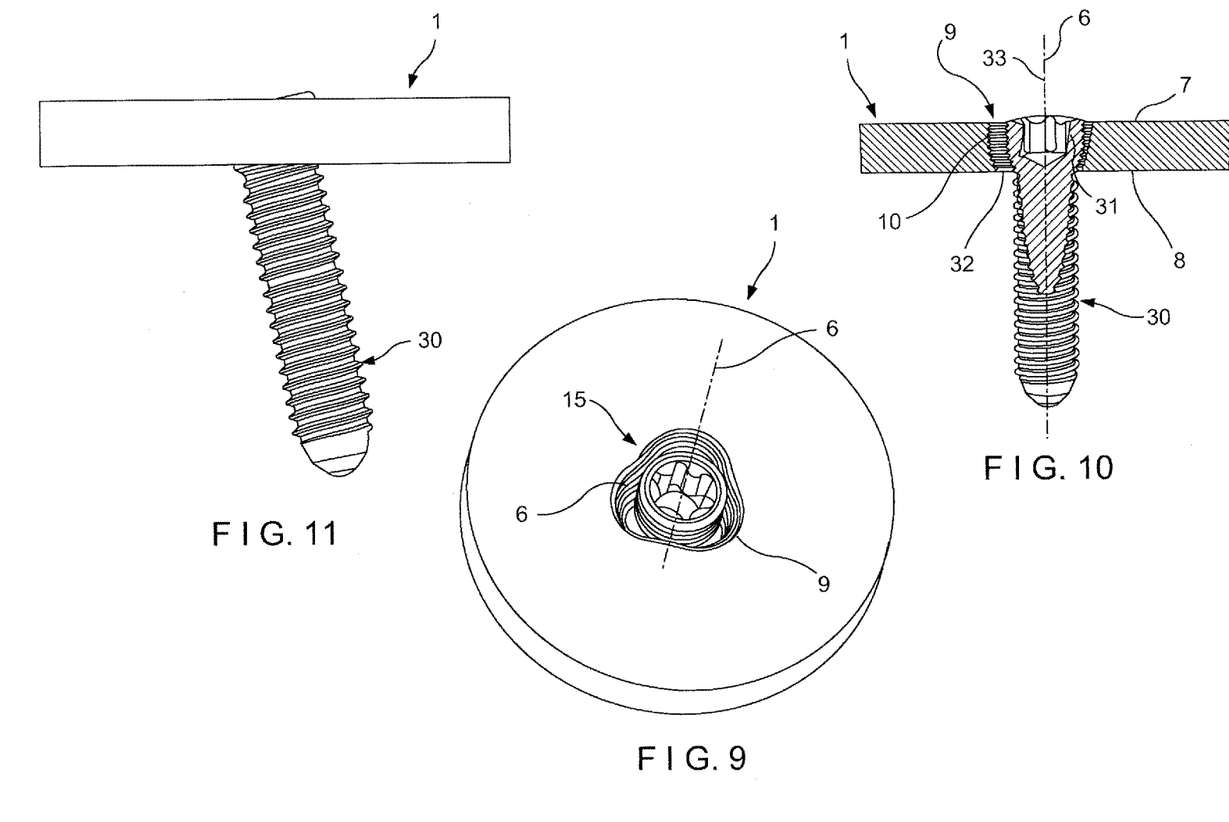
FIG. 9 illustrates a perspective view of another exemplary embodiment of the bone plate according to the present invention.
FIG. 10 illustrates a cross section through the bone plate according to the embodiment of FIG. 9.
FIG. 11 illustrates a lateral view of the bone plate according to the embodiment of FIG. 9.

In FIGS. 9 to 11 another embodiment is illustrated which differs from the embodiment of FIGS. 1 to 8 only in that the generally polygonal through hole 9 comprises rounded corners instead of the N=3 peripheral holes 2 arranged in the corners. Similarly to the embodiment of FIGS. 1 to 8, the wall 10 of the through hole 9 comprises n=3 convex sections 15 which in a cross-section orthogonal to the longitudinal axis 6 are centrally located on the sides of an equilateral triangle. Each of the convex sections 15 is convexly curved in a cross-section orthogonal to the longitudinal axis 6 of the through hole 9 with the apex of each convex section 15 located on a middle line orthogonal to one side of the equilateral triangle. Due to the convex sections 15, a bone screw 30 may be inserted into the through hole 9 under a surgeon selected angle relative to the axis 6.

The through hole 9 includes three radially symmetrically arranged convex sections 15 centrally located on the sides of an equilateral triangle and three concavely rounded sections in the corners of the equilateral triangle. The wall 10 of the through hole 9 therefore comprises n=3 wall portions whereof each wall portion extends along one side of an equilateral triangle and is limited by a transition to a first concavely rounded section at one of its ends and by a transition to a second concavely rounded section at its other end. In the present embodiment each convex section 15 extends over the whole length of the wall portion limited by the transitions. The thread 5 or thread-like structure extends over the whole periphery of the through hole 9. The depth of thread of the thread 5 or thread-like structure can decrease in the concavely rounded sections.

As illustrated in FIG. 10 the through hole 9 tapers towards the distal surface 8 of the bone plate 1. A central bone screw 30 with a screw axis 33 and a screw head 31 is inserted in the through hole 9. The screw head 31 is spherically shaped and comprises an external thread 32 so that the central bone screw 30 can be inserted into the through hole at a user-selected variable angle α between the screw axis 33 and the longitudinal axis 6 of the through hole 9.

Figure 12:
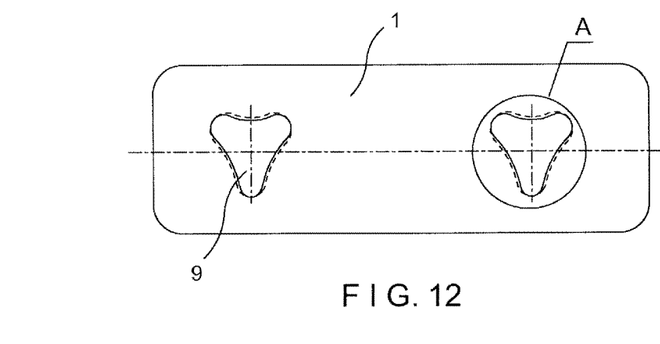
FIG. 12 illustrates a top view onto a further embodiment of the bone plate according to the invention.
Figure 13:
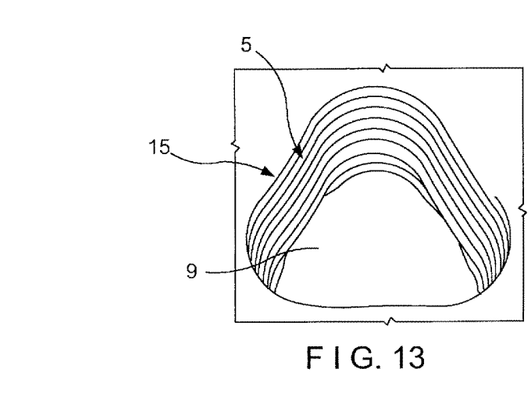
FIG. 13 illustrates a magnified perspective view of detail A in FIG. 12.
Figure 14:
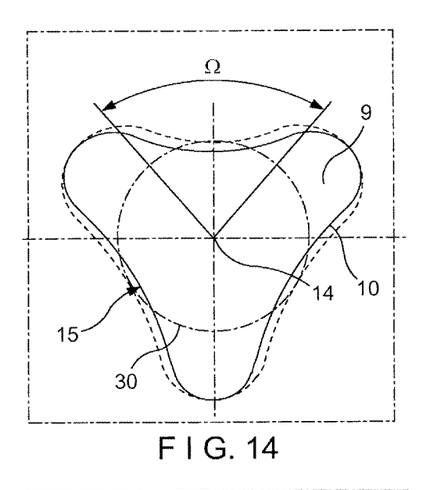
FIG. 14 illustrates a schematic top view of detail A in FIG. 12.

In FIGS. 12 to 14 another embodiment of the bone plate 1 is illustrated which comprises two through holes 9. Similarly to the embodiment of FIGS. 9 to 11, the through hole 9 has cross-sectional area orthogonal to the longitudinal axis 6 with a center 14 located on the longitudinal axis 6 with each of the n=3 convex sections 15 being limited by two radii intersecting each other in the center 14 and enclosing an angle Ω which is smaller than 120°. The wall 10 of each of the two through holes 9 comprises n=3 wall portions with each wall portion extending along one side of an equilateral triangle and limited by a transition to a first concavely rounded section at one of its ends and by a transition to a second concavely rounded section at its other end. Similarly to the embodiment of FIGS. 9 to 11, each convex section 15 extends over the whole length of the wall portion limited by the transitions. The through holes 9 differ from the through hole 9 of the embodiment of FIGS. 9 to 11 only in that the thread 5 or thread-like structure does not extend over the whole periphery of the through hole 9. The depth of thread of the thread 5 or thread-like structure decreases on each end of the convex section 15 at the transition between the convex section 15 and the concavely rounded section in such a way that a portion of the concavely rounded sections is unthreaded.

As illustrated in FIG. 13 the through hole 9 tapers radially inward toward the distal surface 8 of the bone plate 1. Similarly to the embodiment of FIGS. 9 to 11, a central bone screw 30 with a screw axis 33 and a screw head 31 can be inserted in the through hole 9. By using a central bone screw 30 the screw head 31 of which is spherically shaped with an external thread 32, the central bone screw 30 may be inserted into the through hole 9 at a user-selected, variable angle α of the screw axis 33 to the longitudinal axis 6 of the through hole 9.

Figure 15:
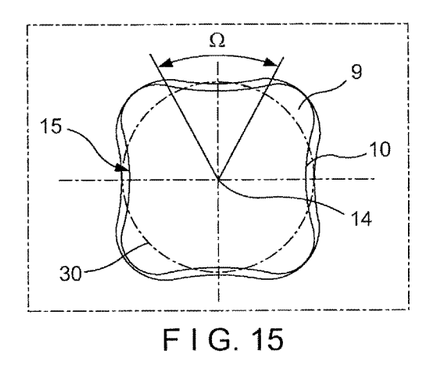
FIG. 15 illustrates a schematic top view onto a further exemplary embodiment of the through hole in the bone plate according to the present invention.

FIG. 15 illustrates a further embodiment of the through hole 9 which differs from the embodiment of FIGS. 12 to 14 only in that it comprises n=4 convex sections 15. Each of the n=4 convex sections 15 is limited by two radii intersecting each other in the center 14 and enclosing an angle Ω which smaller than 90°. The wall 10 of each of the two through holes 9 comprises n=4 wall portions with each wall portion extending along one side of a square and limited by a transition to a first concavely rounded section at one of its ends and by a transition to a second concavely rounded section at its other end. Similarly to the embodiment of FIGS. 9 to 11, each convex section 15 extends over the whole length of the wall portion limited by the transitions. The thread 5 or thread-like structure does not extend over the whole periphery of the through hole 9. The depth of thread of the thread 5 or thread-like structure decreases on each end of the convex section 15 at the transition between the convex section 15 and the concavely rounded section in such a way that a portion of the concavely rounded sections is unthreaded.

Figure 16:
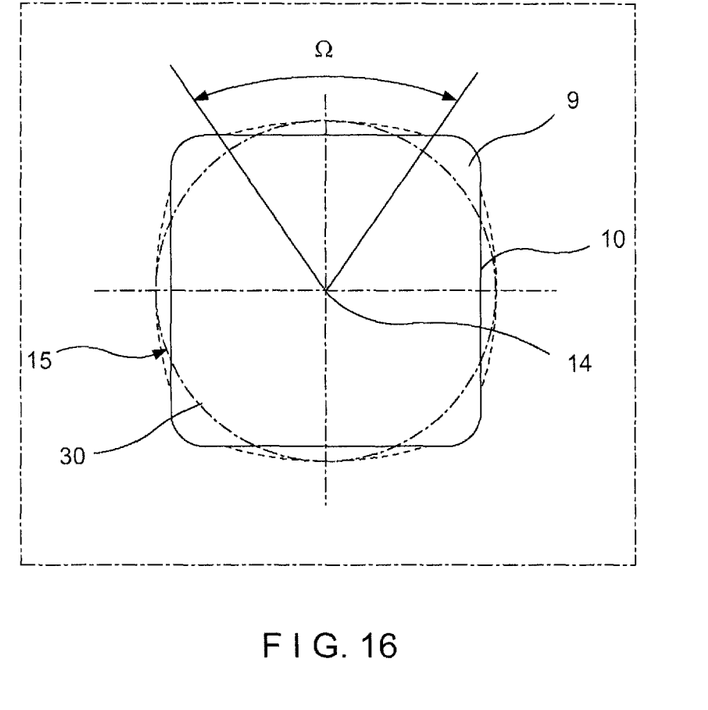
FIG. 16 illustrates a schematic top view onto another exemplary embodiment of the through hole in the bone plate according to the present invention.

FIG. 16 illustrates again a further embodiment of the through hole 9 which differs from the embodiment of FIG. 15 only in that the wall 10 of the through hole 9 comprises n=4 straight sections 15 and that the depth of thread of the thread 5 or thread-like structure decreases from a middle line orthogonal to one side of the square towards the transition between the straight section 15 and each of the concavely rounded sections in such a way that the concavely rounded sections are unthreaded.

Figure 17:
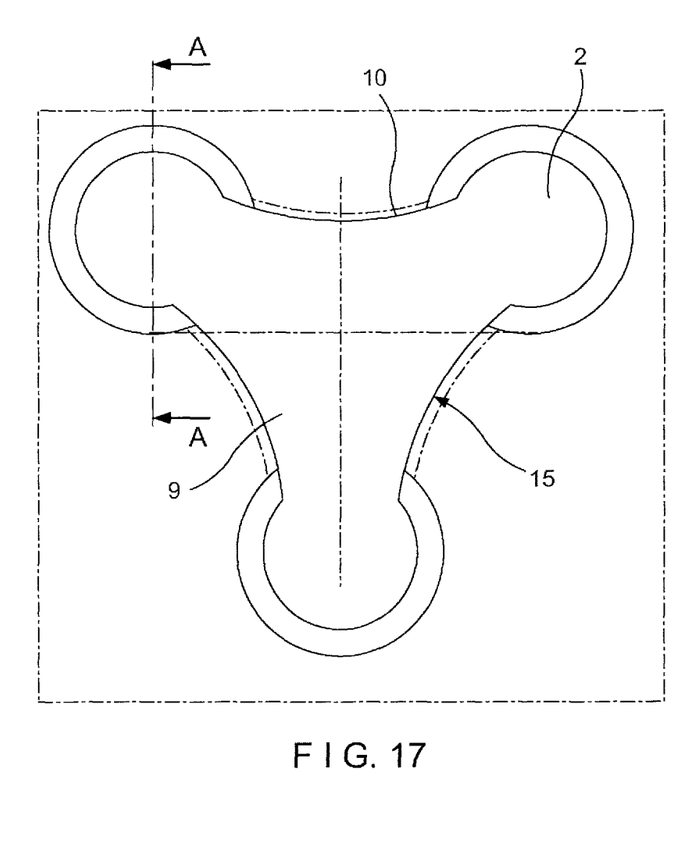
FIG. 17 illustrates a schematic top view onto again another embodiment of the through hole in the bone plate according to the present invention.
Figure 18:
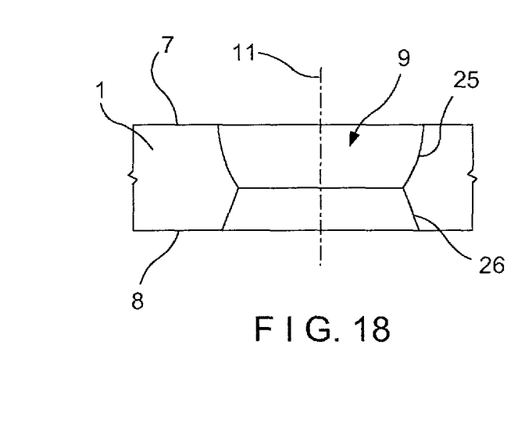
FIG. 18 illustrates a cross-section along line A-A in FIG. 17.

FIGS. 17 and 18 illustrate again a further embodiment of the through hole 9 which differs from the embodiment of FIG. 14 only in that the N=3 peripheral holes 2 are configured to receive conventional cortex screws. Each peripheral hole 2 comprises a spherical recess 25 penetrating partially into the bone plate 1 from the proximal surface 7 and axially adjacent to a conically enlarging lower section 26 extending between the spherical recess 25 and the distal surface 8 of the bone plate 1. Due to the spherical recess 25, a conventional cortex screw with a spherical head may be inserted into each of the peripheral holes 2 at a user-selected angle with respect to the axis 11 of the peripheral hole 2. The n=3 straight or convex sections 15 of the wall 10 of the through hole 9 are configured similarly to the embodiment of FIG. 14.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A bone plate, comprising:
a first through hole extending through the plate along a first longitudinal axis from a proximal surface of the plate to a bone-facing distal surface thereof which, when the plate is placed on a target portion of bone in a desired orientation, faces the bone, an outer wall of the first through hole including three wall sections provided with projections for receiving a screw head of a central bone screw; and
a plurality of first peripheral holes, each of the first peripheral holes extending through the bone plate from the proximal surface to the distal surface thereof along a corresponding first hole axis and including a thread for locking a screw head of a peripheral bone screw therein, each of the first peripheral holes overlapping a periphery of the first through hole to form a composite hole structure configured to receive peripheral bone screws through the first peripheral holes and the central bone screw through the first through hole;
wherein a cross-sectional shape of the three wall sections in a plane including an axis extending orthogonally to a plane including the first longitudinal axis is one of straight and convexly curved toward the first through hole.

2. The bone plate according to claim 1, wherein a cross-sectional shape of the first through hole extending orthogonally to the plane including the first longitudinal axis is polygonal with rounded corners.

3. The bone plate according to claim 1, wherein the first through hole tapers down in size in a direction from the proximal surface towards the distal surface of the bone plate.

4. The bone plate according to claim 1, wherein the projections comprise one of thread and thread-like structure extending over an entire length of each of the wall sections.

5. The bone plate according to claim 4, wherein the one of thread and thread-like structure has a constant depth of thread in the wall sections.

6. The bone plate according to claim 4, wherein a depth of thread of the one of thread and thread-like structure decreases towards proximal and distal ends of each of the wall sections, the depth of thread being greatest at a center portion of the wall sections between the proximal and distal surfaces.

7. The bone plate according to claim 4, wherein a depth of thread of the one of thread and thread-like structure increases toward proximal and distal ends of each of the wall sections, the depth of thread being greatest at a center portion of the wall sections between the proximal and distal surfaces.

8. The bone plate according to claim 1, wherein each of the first peripheral holes comprises a spherical recess partially penetrating the bone plate from the proximal surface.

9. The bone plate according to claim 1, wherein the peripheral bone screws are locked at a fixed angle relative to the corresponding first hole axis and wherein the first through hole includes a thread configured to lock a bone screw inserted therein at an angle relative to the first longitudinal axis selected by a user.

10. The bone plate according to claim 1, wherein each of the first peripheral holes includes a thread configured to lock a peripheral bone screw therein at an angle relative to the corresponding first hole axis selected by a user and wherein the first through hole includes a thread configured to lock a bone screw therein at an angle fixed relative to the first longitudinal axis.

11. The bone plate according to claim 9, wherein the thread extends over at least half of a circumference of each of the first peripheral holes.

12. The bone plate according to claim 1, wherein the first through hole is polygonal and each of the first peripheral holes is arranged at a corner of the first through hole.

13. The bone plate according to claim 12, wherein centers of two adjacent ones of the first peripheral holes are separated by a distance of 4 to 15 mm.

14. The bone plate according to claim 13, wherein the bone plate is made of a CoCr alloy.

15. The bone plate according to claim 12, wherein the first hole axis of a first one of the first peripheral holes oriented relative to the first longitudinal axis at an angle between 5° and 20°.

16. The bone plate according to claim 1, further comprising:
a second through hole, wherein an outer wall of the second through hole includes three wall sections which are one of straight and convex.

17. A bone plate, comprising:
a through hole extending through the plate along a longitudinal axis from a proximal surface to a bone-oriented distal surface which, when the plate is positioned on a bone in a desired orientation, faces the bone, an outer wall of the through hole having N non-concave wall sections provided with projections for lockingly engaging a head of a central bone screw inserted therethrough; and
a plurality of peripheral holes, each of the peripheral holes extending through the bone plate from the proximal surface to the distal surface thereof along a corresponding first hole axis and including a thread for locking a screw head of a peripheral bone screw therein, each of the peripheral holes overlapping a periphery of the first through hole to form a composite hole structure configured to receive peripheral bone screws through the peripheral holes and the central bone screw through the first through hole;
wherein a cross-sectional shape of the wall sections in a plane including an axis extending orthogonally to a plane including the first longitudinal axis is one of straight and convexly curved toward the first through hole.

18. The bone plate according to claim 1, wherein the three wall sections are convex in a direction from the proximal surface to the bone-facing distal surface such that a respective apex of the three wall sections is located radially outside the first through hole.

* * * * *

UNITED STATES PATENT AND TRADEMARK OFFICE
CERTIFICATE OF CORRECTION

PATENT NO. : 9,801,669 B2
APPLICATION NO. : 13/100784
DATED : October 31, 2017
INVENTOR(S) : Roth et al.

It is certified that error appears in the above-identified patent and that said Letters Patent is hereby corrected as shown below:

Claim 17, Column 10, Line 35:
"bone, an outer wall of the through hole having N" should read "bone, an outer wall of the through hole having $N \geq 3$".

Signed and Sealed this
First Day of May, 2018

Andrei Iancu
*Director of the United States Patent and Trademark Office*